United States Patent [19]

Materazzi et al.

[11] Patent Number: 5,190,948
[45] Date of Patent: Mar. 2, 1993

[54] USE OF URIDINE IN THE PHARMACOLOGICAL TREATMENT OF THE PERIPHERAL COMPLICATIONS OF DIABETES

[75] Inventors: Mario Materazzi; Vincenzo Politi; Giovanni Di Stazio; Giovanna De Luca, all of Rome, Italy

[73] Assignee: Polifarma S.p.A., Roma, Italy

[21] Appl. No.: 704,230

[22] Filed: May 22, 1991

[30] Foreign Application Priority Data

Jun. 13, 1990 [IT] Italy .............................. 48057A/90

[51] Int. Cl.$^5$ ............................................ A61K 31/505
[52] U.S. Cl. ................................... 514/274; 514/866
[58] Field of Search ........................................ 514/274

[56] References Cited

PUBLICATIONS

CA 77(3): 14390d, Serra, 1971.
Geiger et al., report presented at the meeting of the Federation of Amer. Societies for Experimental Biol. pp. 93–100, Apr. 1956.
Elrick et al., Metabolism, vol. XI, No. 1, pp. 46–55, Jan. 21, 1961.

Primary Examiner—Frederick E. Waddell
Assistant Examiner—Kimberly R. Jordan
Attorney, Agent, or Firm—Birch, Stewart, Kolasch & Birch

[57] ABSTRACT

Uridine is used to treat the peripheral complications of diabetes, such as neuropathy, retinopathy and vasculopathy, thanks to its characteristics of promotor of glycogen endocellular biosynthesis. 40 diabetic patients were treated for six months with uridine or with placebo in a double-blind clinical teat.

1 Claim, No Drawings

USE OF URIDINE IN THE PHARMACOLOGICAL TREATMENT OF THE PERIPHERAL COMPLICATIONS OF DIABETES

DESCRIPTION

BACKGROUND OF THE INVENTION

1. Field of the Invention

The present invention refers to a new therapeutic use of uridine in the field of peripheral complications in diabetes mellitus.

2. Description of the Prior Art

Uridine is a known endogenous compound which has been studied in the past as a pharmacological agent in many experimental models, even those in no way related to each other. It has, in fact, been shown that cytidine and uridine are capable of prolonging the functional survival of an isolated cat brain. Other researchers have brought to light important anticonvulsive properties of uridine. More recently, uridine has been proposed as a substance promoting sleep, as a substitute for a renal natriuretic system, or as a dopaminergic modulator of the central nervous system.

It is furthermore universally known from classical biochemistry texts that uridine is the most important carrier of glucose within the cell, and that glycogen can only be formed upon intervention of uridine.

It has also been shown that cytidine and uridine are capable of converting the normal use of glucose in cirrhotic patients treated with insulin. It has furthermore been shown that uridine increases the formation of glycogen in the muscles and that uridine can antagonize certain effects due to insulin hypoglycemia.

The peripheral complications in diabetes mellitus include a number of disabling situations, such as neuropathy, retinopathy, vasculopathy, etc. due to the presence in the blood of high quantities of glucose, which can spread passively in all types of cell not provided with specific "carriers".

If the endocellular glucose exceeds the energy requirement, and is not stored in the form of polysaccharides, it can damage the cell, both because it changes into fructose and sorbitol (sugars which do not easily spread outwards, and which for this reason cause the cell to swell and lose functional activity), and because it can react with proteins and nucleic acids, bringing about a form of premature "cell aging".

To relieve the peripheral symptomatology of diabetes mellitus, certain drugs have recently been proposed in the field of therapy. These drugs, by inhibiting the enzyme "aldosoreductase", prevent the glucose from transforming itself into sorbitol, thus limiting the damage caused by cellular oedema (see for example Annual Reports in Medicinal Chemistry 19, 169–177, 1984). At least in short-term clinical tests, these compounds have shown themselves to be of use to antagonize diabetic neuropathies (see for example: Lancet II, 758–762, 1983; New England J. Medicine 316, 599–606, 1987). However, these synthetic derivatives are not without side-effects which could compromise their long-term use, as in theory the diabetic patient would have to be treated all his life. It is therefore necessary to find physiological compounds that, as well as being active, are also free from serious undesirable effects.

SUMMARY OF THE INVENTION

It has now been surprisingly found, and forms the object of the present invention, that uridine possesses these properties and can be used to decrease the peripheral symtomology of diabetes, without causing side-effects even in the case of long-term treatment. Uridine can thus be administered to patients suffering from diabetes mellitus for the pharmacological treatment of peripheral complications such as neuropathy, retinopathy or vasculopathy.

It is thought that the uridine, which is able to enter with ease into the cells, can store the glucose present therein under the form of glycogen.

In order to evaluate at an experimental level the intervention of uridine upon the peripheral symptoms of diabetes, the following experimental tests have been performed.

Experimental Pattern

Forty diabetic patients (25 male and 15 female) were selected, having an average age of 48,5 ± 3,4 years, with a medical history of at least 5 years of diabetes, showing a reduction of the speed of motorial conductivity (VCM), and of the speed of sensorial conductivity (VCS) in at least one peripheral nerve, persistent pain in the lower limbs, reduction of the threshold of vibration perception.

After having undergone a "wash-out" period of two weeks, to suspend all pharmacological treatment that might interfere with the evaluation of the parameters to be examined, the patients were divided randomly into two groups: the first group received 300 mg of uridine three times per day; the second group received similar capsules containing placebo. Neither the patients nor the doctors knew who was being treated with placebo and who with uridine (double-blind test). Treatment continued for 180 consecutive days.

Clinical and neurophysiological evaluation took place at the following times: prebasal, basal (after two weeks "wash-out"), at 60 days, 120 days and 180 days, and after 90 days from the end of treatment as a follow-up. All patients were evaluated after a general and neurological check-up, ECG (electrocardiogram), haematological, urine and glycosilate haemoglobin (HnAlc) tests. The statistical calculation was carried out using the Student test and with the two-way Anova test.

Results

None of the patients had to suspend treatment due to side-effects, and this gives an indication of the optimum toleration of uridine, a fact which can also be seen from the absence of significant differences between the two groups as far as the haematological, ECG, urinary and glycosilate haemoglobin tests are concerned.

The statistical test showed differences both in the VCM and in the VCS. These differences became significant at the 120th day and remained so both at the 180th and during the follow-up period.

TABLE 1

Average VCM ± SD (m/sec) of the SPE in diabetics treated with uridine and with placebo.

|  | URIDINE | PLACEBO | Student | Anova |
| --- | --- | --- | --- | --- |
| Pre-basal | 38.1 + 1.8 | 38.4 + 2.3 | N.S. | N.S. |
| Basal | 37.4 + 2.3 | 38.0 + 2.7 | N.S. | N.S. |
| Day 60 | 37.7 + 2.2 | 38.1 + 2.4 | N.S. | N.S. |
| Day 120 | 40.9 + 2.4 | 38.2 + 2.4 | p < 0.05 | p < 0.01 |
| Day 180 | 43.5 + 1.9 | 38.6 + 2.4 | p < 0.01 | p < 0.001 |

TABLE 1-continued

Average VCM ± SD (m/sec) of the SPE in diabetics treated with uridine and with placebo.

|  | URIDINE | PLACEBO | Student | Anova |
|---|---|---|---|---|
| Follow-up | 43.0 + 1.4 | 38.4 + 2.5 | $p < 0.05$ | $p < 0.001$ |

SPE = outer sciatic popliteal nerve
SD = standard deviation

TABLE 2

Average VCM ± SD (m/sec) of the SPI in diabetics treated with uridine and with placebo.

|  | URIDINE | PLACEBO | Student | Anova |
|---|---|---|---|---|
| Pre-basal | 34.9 + 2.1 | 35.3 + 2.4 | N.S. | N.S. |
| Basal | 34.8 + 1.6 | 34.9 + 1.8 | N.S. | N.S. |
| Day 60 | 35.7 + 1.8 | 35.5 + 1.9 | N.S. | N.S. |
| Day 120 | 39.5 + 2.1 | 35.4 + 2.7 | $p < 0.005$ | $p < 0.005$ |
| Day 180 | 42.4 + 1.6 | 35.8 + 1.7 | $p < 0.0005$ | $p < 0.001$ |
| Follow-up | 41.3 + 1.1 | 35.3 + 2.1 | $p < 0.001$ | $p < 0.001$ |

SPI = inner sciatic popliteal nerve

TABLE 3

Average amplitude ± SD (microV) of the motorial response of the SPI in diabetics treated with uridine and with placebo.

|  | URIDINE | PLACEBO | Student | Anova |
|---|---|---|---|---|
| Pre-basal | 6.3 + 3.2 | 6.2 + 2.7 | N.S. | N.S. |
| Basal | 6.1 + 2.6 | 6.1 + 2.4 | N.S. | N.S. |
| Day 60 | 6.4 + 2.6 | 6.3 + 2.5 | N.S. | N.S. |
| Day 120 | 7.4 + 2.8 | 6.4 + 2.2 | N.S. | $p < 0.01$ |
| Day 180 | 8.7 + 3.0 | 6.2 + 2.4 | $p < 0.05$ | $p < 0.01$ |
| Follow-up | 8.5 + 3.1 | 6.1 + 2.2 | $p < 0.05$ | $p < 0.01$ |

TABLE 4

Average VCM ± SD (M/sec) of the sural nerve in diabetics treated with uridine and with placebo.

|  | URIDINE | PLACEBO | Student | Anova |
|---|---|---|---|---|
| Pre-basal | 32.6 + 3.0 | 32.7 + 3.2 | N.S. | N.S. |
| Basal | 32.8 + 2.0 | 33.0 + 2.5 | N.S. | N.S. |
| Day 60 | 34.0 + 2.3 | 32.9 + 2.0 | $p < 0.05$ | $p < 0.01$ |
| Day 120 | 37.2 + 2.2 | 33.4 + 2.6 | $p < 0.005$ | $p < 0.001$ |
| Day 180 | 41.1 + 2.2 | 33.0 + 2.3 | $p < 0.001$ | $p < 0.001$ |
| Follow-up | 40.1 + 1.7 | 33.2 + 2.2 | $p < 0.005$ | $p < 0.001$ |

TABLE 5

Average amplitude ± SD (microV) of the SAP of the sural nerve in diabetics treated with uridine and with placebo.

|  | URIDINE | PLACEBO | Student | Anova |
|---|---|---|---|---|
| Pre-basal | 4.5 + 1.9 | 4.7 + 2.3 | N.S. | N.S. |
| Basal | 4.4 + 1.8 | 4.8 + 2.4 | N.S. | N.S. |
| Day 60 | 4.9 + 2.0 | 4.6 + 2.1 | N.S. | N.S. |
| Day 120 | 5.9 + 2.0 | 4.7 + 1.9 | $p < 0.05$ | $p < 0.05$ |
| Day 180 | 7.0 + 2.4 | 4.7 + 2.2 | $p < 0.001$ | $p < 0.01$ |
| Follow-up | 6.7 + 1.7 | 4.9 + 2.2 | $p < 0.005$ | $p < 0.01$ |

SAP = potential of sensorial action

Conclusions

The results reported above show that uridine is capable of reducing the entity of complications in diabetes mellitus in a group of patients treated for 6 months with the drug. The study was performed using a double-blind test and the results are derived from objective measures. It can thus be concluded that uridine, probably by means of the biosynthesis of glycogen within the cells, limits the damage caused by high levels of glucose, and can thus be used in the treatment of peripheral disturbances in diabetes, such as retinopathy, vasculopathy, etc.

The daily dose can vary between 500 and 2000 mg per day of uridine taken orally and the dose can be administered using the normal pharmaceutical forms.

We claim:

1. A method for the pharmaceutical treatment of patients suffering from peripheral neuropathy, retinopathy or peripheral vasculopathy produced in said patients by diabetes mellitus as a peripheral complication, comprising administering orally to said patients a pharmaceutical effective amount of uridine to reduce said peripheral complications, with the proviso that cytidine is not administered.

* * * * *